(12) United States Patent
Sabovic et al.

(10) Patent No.: US 10,048,513 B2
(45) Date of Patent: Aug. 14, 2018

(54) CONTINUOUS AUTOFOCUSING EYEWEAR

(71) Applicant: Focure Inc., San Francisco, CA (US)

(72) Inventors: Nebojsa Sabovic, San Francisco, CA (US); Reed Foster, San Francisco, CA (US)

(73) Assignee: Focure Inc., San Francisco, CA (US)

( * ) Notice: Subject to any disclaimer, the term of this patent is extended or adjusted under 35 U.S.C. 154(b) by 0 days.

(21) Appl. No.: 15/341,992

(22) Filed: Nov. 2, 2016

(65) Prior Publication Data

US 2017/0123233 A1    May 4, 2017

Related U.S. Application Data

(60) Provisional application No. 62/249,817, filed on Nov. 2, 2015.

(51) Int. Cl.
| | |
|---|---|
| *G02C 7/08* | (2006.01) |
| *A61B 3/14* | (2006.01) |
| *A61B 3/113* | (2006.01) |
| *G02C 7/06* | (2006.01) |
| *A61B 3/08* | (2006.01) |

(52) U.S. Cl.
CPC ............ *G02C 7/083* (2013.01); *A61B 3/08* (2013.01); *A61B 3/113* (2013.01); *A61B 3/145* (2013.01); *G02C 7/06* (2013.01); *G02C 7/08* (2013.01); *G02C 7/081* (2013.01)

(58) Field of Classification Search
CPC .......... G02C 7/083; G02C 7/081; G02C 7/08; G02C 7/06; G02C 7/088; A61B 3/08; A61B 3/113; A61B 3/14; A61B 3/145
USPC ......................................... 351/159.39, 159.4
See application file for complete search history.

(56) References Cited

U.S. PATENT DOCUMENTS

| | | | | |
|---|---|---|---|---|
| 4,836,670 | A * | 6/1989 | Hutchinson | A61B 3/113 351/210 |
| 4,950,069 | A * | 8/1990 | Hutchinson | A61B 3/113 351/210 |
| 4,973,149 | A * | 11/1990 | Hutchinson | A61B 3/113 351/210 |
| 5,220,361 | A | 6/1993 | Lehmer | |
| 5,408,292 | A | 4/1995 | Kumakura | |
| 5,532,784 | A | 7/1996 | Nishimura | |
| 5,861,936 | A | 1/1999 | Sorensen | |
| 6,095,989 | A * | 8/2000 | Hay | A61B 3/0025 600/558 |
| 6,419,638 | B1 * | 7/2002 | Hay | A61B 3/0025 600/558 |
| 7,286,753 | B2 | 10/2007 | Yamasaki | |

(Continued)

FOREIGN PATENT DOCUMENTS

| | | |
|---|---|---|
| WO | 2017079342 A1 | 5/2017 |
| WO | 2017079343 A1 | 5/2017 |

OTHER PUBLICATIONS

PCT International Search Report_PCT/US2016/060174_dated Mar. 24, 2017.

(Continued)

*Primary Examiner* — William R Alexander
(74) *Attorney, Agent, or Firm* — Daylight Law, P.C.

(57) ABSTRACT

Autofocusing eyewear for correcting eye accommodative dysfunctions includes a pupil tracking VOG (video-oculography) system to determine location of the pupils, a focus-tunable lens and a controller to focus the lens based on the position of the pupils.

13 Claims, 6 Drawing Sheets

(56) References Cited

U.S. PATENT DOCUMENTS

| | | | |
|---|---|---|---|
| 7,322,699 B2* | 1/2008 | Barth | A61B 3/1005 351/205 |
| 7,600,873 B2 | 10/2009 | Grundig | |
| 7,654,668 B2 | 2/2010 | Neuhann | |
| 8,939,579 B2 | 1/2015 | Agurok | |
| 8,955,973 B2 | 2/2015 | Raffle | |
| 2005/0024586 A1 | 2/2005 | Teiwes | |
| 2007/0279584 A1 | 12/2007 | Howell | |
| 2010/0157178 A1 | 6/2010 | Macnaughton | |
| 2011/0228975 A1* | 9/2011 | Hennessey | A61B 3/113 382/103 |
| 2012/0127062 A1 | 5/2012 | Bar-Zeev | |
| 2012/0133891 A1 | 5/2012 | Jiang | |
| 2012/0194781 A1* | 8/2012 | Agurok | A61B 3/113 351/201 |
| 2013/0241805 A1* | 9/2013 | Gomez | G09G 3/003 345/8 |
| 2013/0286178 A1 | 10/2013 | Lewis | |
| 2014/0285905 A1 | 9/2014 | Zhou et al. | |
| 2014/0375788 A1 | 12/2014 | Gabara | |
| 2015/0185503 A1 | 7/2015 | Tate | |
| 2015/0220779 A1 | 8/2015 | Publicover | |
| 2015/0243101 A1 | 8/2015 | Schowengerdt | |

OTHER PUBLICATIONS

PCT International Search Report_PCT/US2016/060175_dated Jan. 19, 2017.
D. Li, et al., "Starburst: A Hybrid Algorithm for Video Based Eye Tracking Combining Feature Based and Model Based Approaches", Proc. of the IEEE Vision for Human Computer Interaction Workshop at CVPR, 2005.
H. Ren, et al., "Tunable-Focus Flat Liquid Crystal Spherical Lens", Applied Physics Letters, vol. 84, No. 23, pp. 4789-4791, Jun. 7, 2004.
R. Valenti, et al., "Accurate Eye Center Location Through Invariant Isocentric Patterns", IEEE Trans. Pattern Analysis and Machine Intelligence, vol. 34, No. 8, pp. 1785-1798, 2012.
S. Shian, et al., "Tunable Lenses Using Transparent Dielectric Elastomer Actuators", Optics Express, vol. 21, No. 7, pp. 8669-8676, Apr. 8, 2013.
PCT International Preliminary Report on Patentability_PCT/US2016/060174_dated May 8, 2018.
PCT International Preliminary Report on Patentability_PCT/US2016/060175_dated May 8, 2018.
Office Action dated Jun. 11, 2018 for U.S. Appl. No. 15/342,010.

* cited by examiner

CONTINUOUS AUTOFOCUSING EYEWEAR

CROSS-REFERENCE TO RELATED APPLICATIONS

This application claims benefit of priority of U.S. Provisional Application Ser. No. 62/249,817, filed Nov. 2, 2015, which is incorporated herein by reference in its entirety for all purposes.

BACKGROUND

Presbyopia is an age-related farsightedness condition caused by a loss of elasticity in the lens of the eye. This loss of elasticity decreases an adult's ability to accommodate near objects. Children typically have the ability to accommodate 20 dioptres or focus on any object from 50 mm from their eye to infinity. Most adults, by age 50, can only accommodate 2 dioptres. This loss of ability to accommodate generally results in adults requiring some form of visual correcting such as reading glasses to focus on near objects. This means that adults must wear reading glasses to accommodate near objects and then remove them to accommodate far objects. In cases where adults also require glasses to correct nearsightedness (inability to accommodate far objects) they must switch between two sets of glasses depending on the depth of their gaze. This is a cumbersome solution for coping with presbyopia as well as myopia and hyperopia. Users would benefit massively from eyewear that adjusted automatically to accommodate near and far objects without requiring manual input from the user.

Several eyewear products have been developed to help adults accommodate both near and far objects using a couple different kinds of lenses. Adlens offers a pair of glasses that uses manually tunable Alvarez lenses that the user can adjust by twisting a knob on each lens. Pixeloptics developed glasses that allow the user to manually switch between two forms of correction (a farsightedness correction and a nearsightedness correction) by pressing a button. Pixeloptics also made a product that uses an accelerometer to allow the user to manually adjust between near and far prescriptions by moving their head. Eyejusters also produced eyewear that allows the user to manually focus Alvarez lenses. Adlens developed eyewear with a membrane lens for continuous focus accommodation that also requires the user to manually adjust a knob on the glasses in order to focus on near or far objects. None of these technologies allows for automatic continuous focus adjustment, but instead rely on a user to engage the focus mechanism.

In order for eyewear to make automatic adjustments to a continuous focus lens, it needs to observe the eye and determine the depth of the user's gaze. There are features of the eye, specifically the relative position of the pupils, that can be used to determine depth of gaze. Sorensen proposed using a neural network to process reflections from the eye to provide an at least partially in focus image in a display screen. (U.S. Pat. No. 5,861,936) The current disclosure includes cameras and a computer controller to track the pupils and determine the depth of gaze using a technique known as video-oculography (VOG). Agurok et al dismisses the idea of using VOG parallax tracking to determine depth of gaze based on the assumption that the technology would be slow and the eyewear cumbersome and heavy. (U.S. Pat. No. 8,939,579) There is a need, therefore for a VOG parallax tracking system with a continuous focus lens and a computer controller to allow the user to focus automatically between near and far objects.

SUMMARY

The present invention is related to autofocusing eyewear for correcting eye accommodative dysfunctions including, but not limited to, presbyopia, myopia, hyperopia, astigmatism and asthenopia. The eyewear comprises a pupil tracking VOG (video-oculography) system to determine location of the pupils, a focus-tunable lens and a controller to focus the lens based on the position of the pupils. Whereas prior-art gaze-tracking systems used Purkinje points, (U.S. Pat. No. 8,939,579), which are sensitive to outside lighting and difficult to use reliably, the present system is able to look at the features of the eye itself to determine the pupil location.

The invention helps the conditions where the person needs different focal power (for each eye) for looking at the various distances. For instance, for presbyopia, the correction of the lens is the strongest for short distances. For asthenopia, the user might choose to help the muscles in their eye by doing some correction when looking at short distances for a long while. The invention can also be used as traditional glasses and provide a single corrective power, and use the calibration mechanism to customize the degree of correction either to a single setting or to various settings based on some other input, such as the time of day, or an input provided remotely to the eyewear by a nearby device.

The video-oculography system captures images of the eye using a sensor, such as a CMOS sensor. A diffuse illumination system can be present to help the camera operate in low-light conditions, and the camera and such illumination system can operate in the infrared range, so as to not interfere with the operation of the eye.

The controller processes the image using a pupil-detection algorithm, such as the one described in R. Velenti, T. Gevers, "Accurate eye center location through invariant isocentric patterns", *IEEE Trans. Pattern Analysis and Machine Intelligence*, Vol. 34, No. 8, pp. 17851798, 2012 and D. Li, D. Winfield, D. Parkhurst, "Starburst: A hybrid algorithm for video based eye tracking combining feature based and model based approaches", Proceedings of the IEEE Vision for Human Computer Interaction Workshop at CVPR, 18, 2005, or other, to produce X and Y coordinates of the pupil center, and/or the eccentricity of the pupil's image in the camera. The controller then uses this data, together with data provided during calibration, to calculate the desired focal power for the lens. This calculation can be either done piecewise, by calculating the angles of both pupils, calculating the distance at which they intersect, and applying the focal power associated with that distance; or directly, by mapping pupil coordinates to focal powers. This and any other required mappings can be obtained in the calibration phase, which can either happen before the device is used, or can be incorporated in the regular usage by using user feedback.

The lens is any focus-tunable lens, such as an electromechanical lens (which use electrical motors or electroactive polymers to move or reshape solid, flexible or Alvarez lens) or liquid-crystal lens. As used herein, an Alvarez lens is a lens in which two wave-shaped polycarbonate plates are configured to glide across each other, thus adjusting the power of the lens. The lens may also include a fixed lens, such as an astigmatism-correcting lens.

Certain exemplary embodiments utilize an elastomer-liquid lens system which makes use of an inline, transparent electroactive polymer actuator, including a passive membrane, a dielectric elastomer actuator membrane, and a clear liquid. The electroactive membrane is a transparent dielectric elastomer coated with transparent compliant electrodes on both sides. In certain embodiments the dielectric elastomer can be a commercially available acrylic elastomer and the electrodes are single walled carbon nanotube. (Shian et al., *Optics Express*, Vol 21 No. 7, pp 8669-8676, 8 Apr. 2013) The focal length and the numerical aperture of the lens in the rest state are determined by both the refractive index of the liquid and the extent of the membrane bulging. The latter is controlled by the volume of the liquid placed in inside the cavity; more liquid reduces the focal length and increases the numerical aperture of the lens. The focal length of the lens can be designed to increase or decrease upon actuation depending on the location of the electroactive membrane, i.e., as the larger or smaller diameter membrane, respectively.

Tunable focus flat liquid crystal spherical lenses can also be used in certain embodiments. An example of such a lens is a tunable-focus spherical lens using two flat substrates and inhomogeneous electric field over a homogeneous liquid crystal layer as described by Ren et al., Applied Physics Letters, Vol 84, No. 23, pp 4789-4791, 7 Jun. 2004. The top flat substrate has an imbedded spherical indium-tin-oxide electrode and the bottom has a planar ITO electrode on its inner surface. The inhomogeneous electric field generates a centrosymmetric gradient refractive index profile within the LC layer which causes the focusing behavior. The focal length of the LC lens can be tuned continuously from infinity to 0.6 m by the applied voltage. Any other appropriate lens systems known in the art are contemplated by the present disclosure. The lens of any of the described systems can also include a fixed lens, such as an astigmatism-correcting lens.

In addition to auto-focusing eyeglasses, the current disclosure is also useful for screen gaze tracking to identify the position on a screen at which a person looking, virtual or augmented reality, for tracking position and/or depth of gaze, eye typing, surgical applications such as tracking eyes during surgery and medical testing for eye abnormalities and prescription determination, among others that would be apparent to persons of skill in this art.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
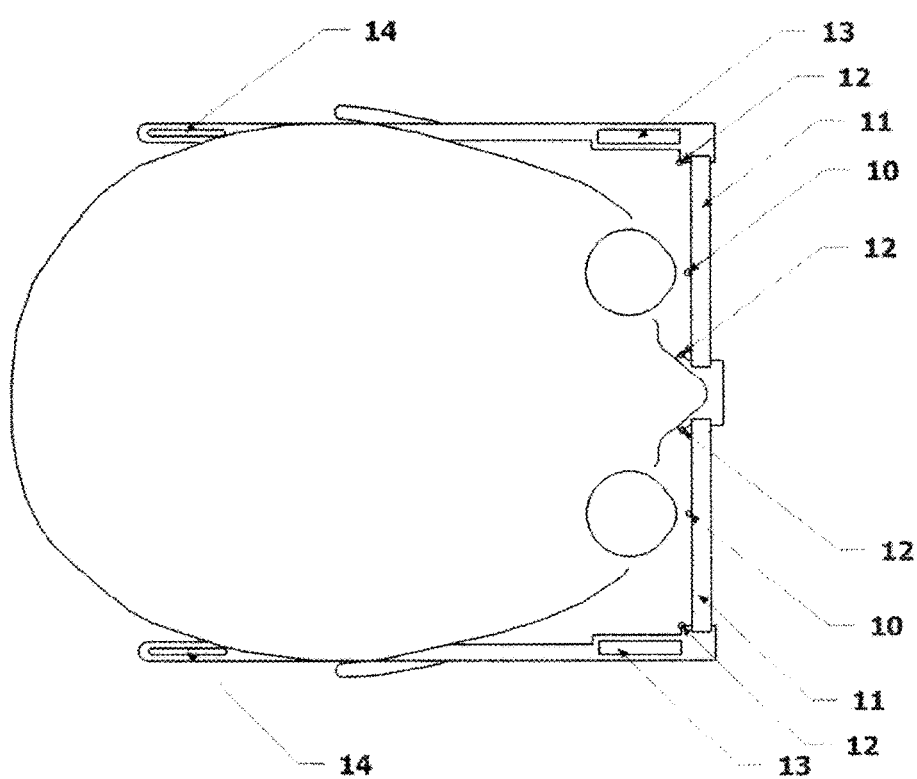
FIG. 1 is a schematic drawing of an embodiment of an imaging subsystem 10, lenses subsystem 11, illumination subsystem 12, controller subsystem 13, battery subsystem 14 and user's eyes, nose and head.

The primary components of an embodiment of autofocusing eyewear are shown schematically in FIG. 1. In this diagram, there are two CMOS sensors forming the imaging subsystem 10, two variable-power lenses forming the lenses subsystem 11, four wide-angle IR LED lights forming the illumination subsystem 12, controller electronics forming the controller subsystem 13 and the battery subsystem 14 which powers all the other subsystems. These subsystems 10, 11, 12, 13 and 14 are all mounted on an eyeglass frame.

The imaging subsystem 10 is connected to the controller subsystem 13 and provides the image of the eye to be used for determining the depth of gaze. The lens subsystem 11 is connected to and controlled by the controller subsystem 13 and its role is to change the focus of the lens subsystem 11 in accordance with user's depth of gaze. The illumination subsystem 12 is connected to and controlled by the controller subsystem 13 and ensures that a clear picture of the eye is available in all light conditions. The controller subsystem 13 is responsible for processing the imaging subsystem 10 inputs and controlling the lenses subsystem 11 and illumination subsystem 12. The battery subsystem 14 is connected to all the other subsystems 10, 11, 12 and 13.

Figure 2:
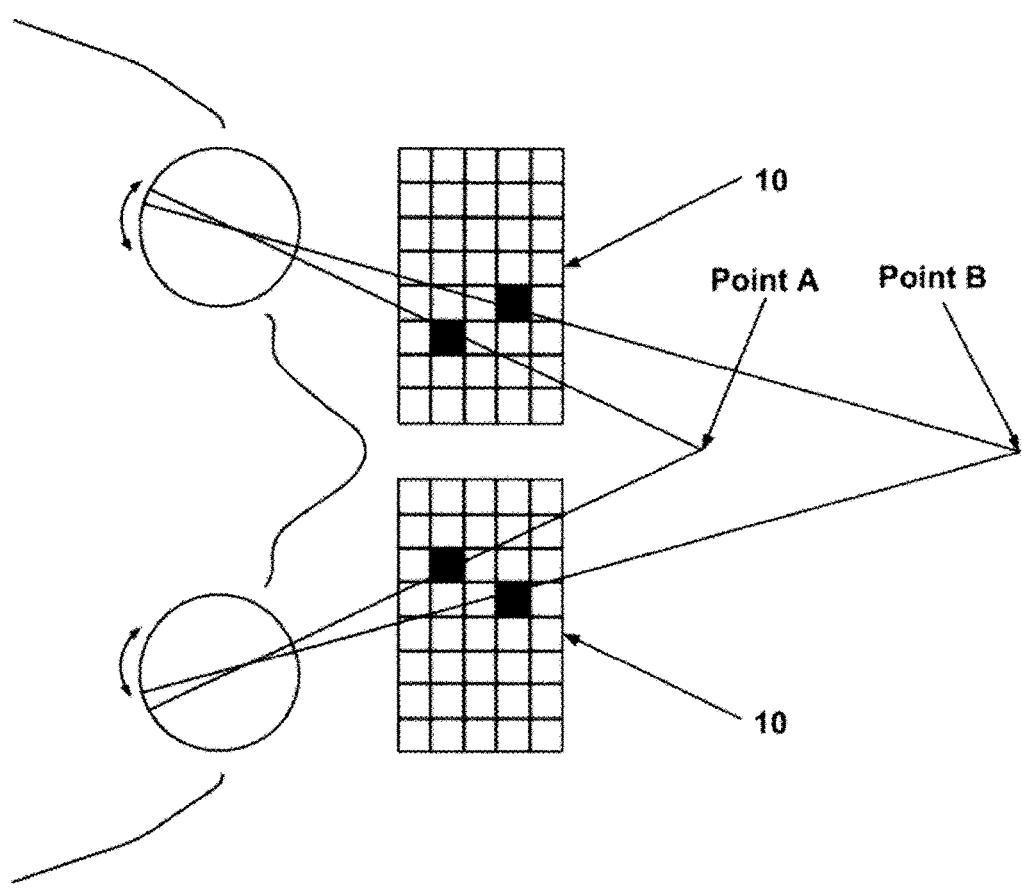
FIG. 2 is a schematic drawing illustrating a function of the imaging subsystem 10 at two different depths of the user's gaze at point A and point B.

The method of operation is based on the following observation. When the user looks at a point A, the eyes rotate so that the two lines originating in each eye's fovea centralis and going through the pupils intersect at that point A. FIG. 2 shows that the position of the image of the pupil in the sensor uniquely determines the point A that the user is looking at.

By using a process described below, the controller 13 determines the depth of the user's gaze from the positions of the pupils.

Figure 3:
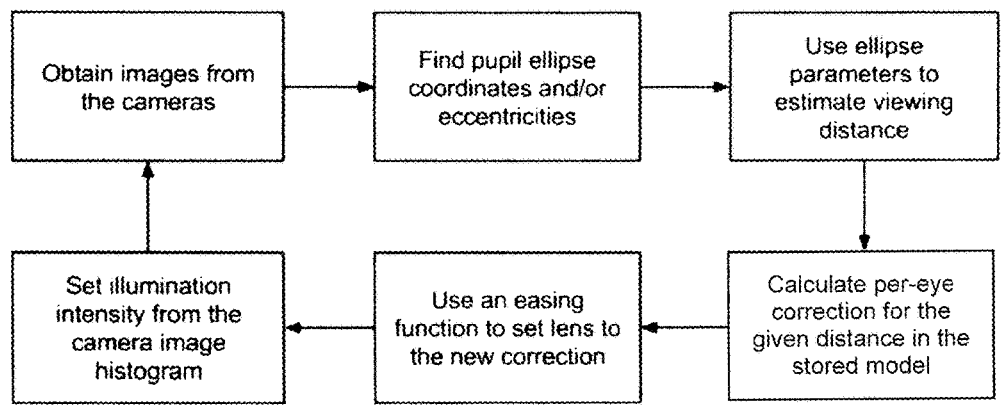
FIG. 3 is a sequence of steps that the eyewear executes in order to detect the gaze depth and adjust the focal power of the lenses.

The controller 13 continuously runs a loop shown on schematic diagram on FIG. 3 from 5 to 200 times per second or in certain embodiments, about fifty times per second to determine the depth of the user's gaze and focus the lenses 11 accordingly.

Figure 4:
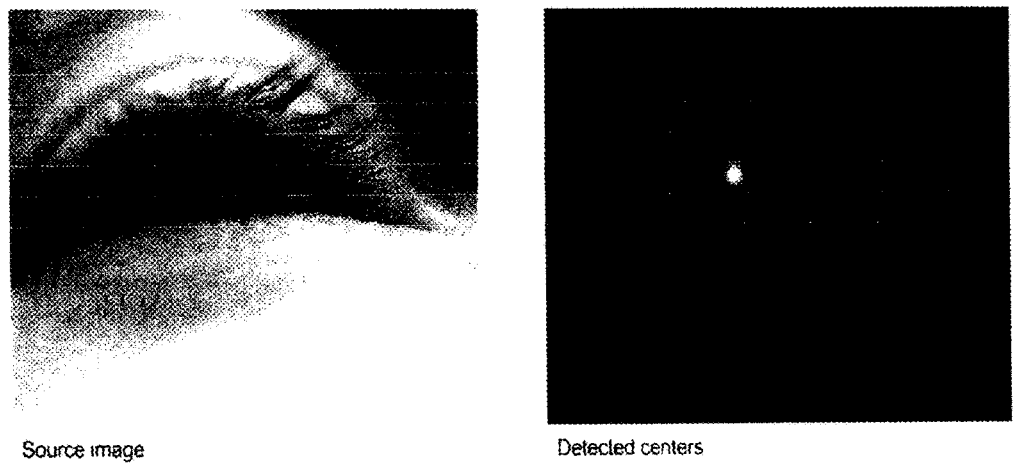
FIG. 4 shows the detected pupil center from the image.
Figure 5:
FIG. 5 shows the result of the detection of the ellipse of the pupil.

First, the images from the imaging subsystem 10 are processed by the controller 13 to find the centers of the pupils, and/or the eccentricities of the elliptical projections of pupils onto the CMOS sensors. Many algorithms exist for this purpose, such as the ones described in Velenti, 2012 and Li, 2005. The algorithms are combined so as to use a more precise algorithm to find the centers of the pupils (Velenti, 2012), and then switch to a different algorithm (Li, 2005) to find the parameters of the ellipses. An example output of the algorithm for finding the pupil centers shows the probability of each point being the center in FIG. 4. FIG. 5 shows that the projection of the pupil is an ellipse whose eccentricity depends on the angle of the rotation of the eye.

Then, these coordinates are used to obtain the viewing distance. The precision of the result varies with the complexity of the method. Our research, shown on FIG. 6, has shown sufficient accuracy close to the optical axis with even the simplest linear model which just matches X coordinates of the left ($X_l$) and right ($X_R$) pupils with the distance:

$$d=d(X_R-Xd)$$

Figure 6:
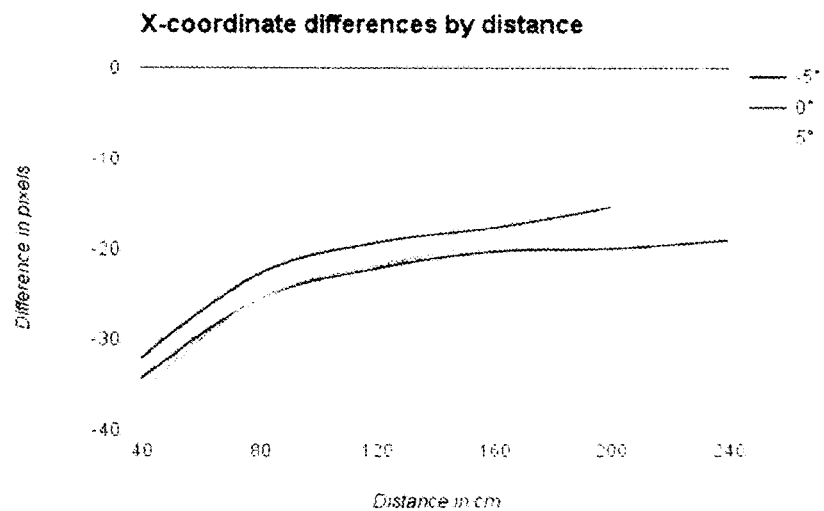
FIG. 6 is the function d that maps the depth of gaze (measured in cm from the eye) to the distance of pupil centers in the left and right eyes (measured in pixels).
Figure 7:
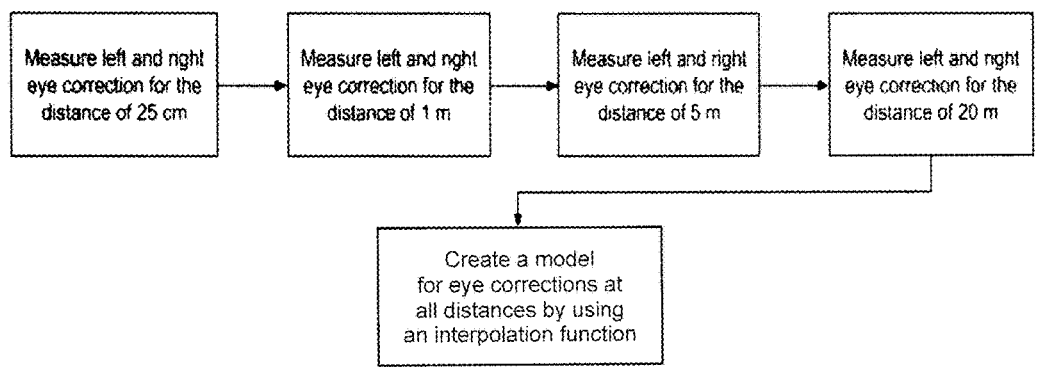
FIG. 7 shows a sequence of steps executed in an example calibration stage before the device is used.

The function d, for a test user, is shown in FIG. 6. This function d is dependent on the eye anatomy and varies significantly from user to user. To obtain function d, we use the process of calibration. An example calibration method would be to ask the user to look at objects at predetermined distances (we used 0.4 m, 0.8 m, 1.2 cm, 1.6 m and 2 m). Pupil coordinates are sampled at these distances, and the function d is obtained by spline interpolation for each distance in between, allowing a mapping of the curve of pupil distance and gaze depth.

The function d, can use a geometrical model of the eye, and use calibration data to determine parameters of the model such as eye radius, interpupilary distance and position of the eyes relative to the glasses.

To focus the lenses 11, we need to know the focal power needed by the user at each distance. In this example calibration method, we would also ask the user to enter the focal power required for each of the predetermined distances. This produces a mappings $P_L$ and $p_R$ of focal powers from the distance d:

$$p_L=P_L(d)=h(d(X_R-X_l))$$

$$PR\ PR(d)P_R(d(X_R-XL))$$

These two steps can be combined into one, as shown on FIG. 6. The calibration can run once, before the eyewear is used for the first time. This would specify the functions:

$$PL=PZXR^{108}\ X)$$

$$P_R=p_R(X_R-/K)$$

Figure 8:
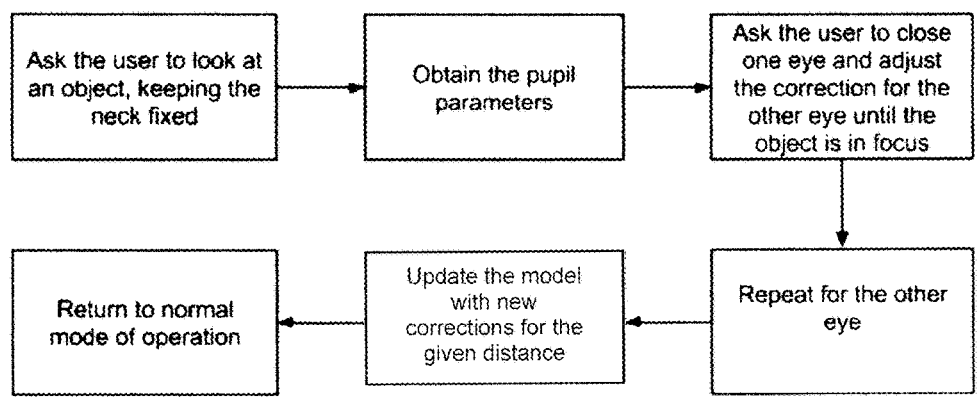
FIG. 8 shows a sequence of steps executed in incremental calibration.

The preferred embodiment instead uses incremental calibration. The autofocusing eyewear has a BLUETOOTH® connection which is used with a smartphone or a computer to initiate calibration mode. Whenever the user sees an object that is not in focus, the user enters the calibration mode. In this mode, the device follows the steps listed in FIG. 8. The user looks at the object that is not in focus, and uses the smartphone or the computer to adjust the correction for the left and right eye until the object is in focus. This adds a point in each of the mappings p, and, improving the accuracy of the eyewear.

Once the device is calibrated and the functions $p_i$, and PR are known, the device is able to plug in the values for the pupil location and obtain the desired corrective power for each lens 11 for the depth of user's current gaze. The controller subsystem 13 does that many times in a second, and directs the lenses subsystem 11 to change the focal power to the desired corrective power. To minimize focusing jitter, an easing function is used.

Figure 9:
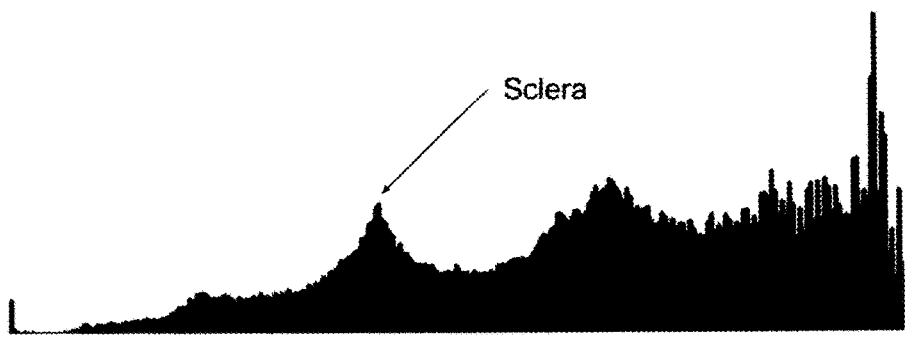
FIG. 9 is a histogram of the pixel intensities in an image of the eye made by an IR CMOS sensor.

Since the accuracy of the pupil-finding algorithm depends on the cumulative illumination of the eye, the controller subsystem 13 also calculates the histogram of the pixel intensities of the image of the eyes captured by the imaging subsystem 10 to adjust the intensity of the illumination subsystem 12 so as to use the minimum illumination in which the eye is clearly discernible by the imaging subsystem 10. FIG. 9 shows a typical histogram of an IR CMOS sensor picture of the eye. The sclera is clearly visible as a peak on this histogram, and its position in the histogram is used to control illumination.

All of the apparatus, components and methods disclosed and claimed herein can be made and used without undue experimentation in light of the present disclosure. While the apparatus, components and methods of this invention have been described in terms of preferred embodiments, it will be apparent to those of skill in the art that variations may be applied to the construction or components described herein without departing from the concept, spirit and scope of the invention. All such similar substitutes and modifications apparent to those skilled in the art are deemed to be within the spirit, scope and concept of the invention as defined by the appended claims.

The invention claimed is:

1. A method of providing passively improved vision to a user, the method comprising the steps of:
   providing an eyewear device, said device comprising:
      an imaging subsystem;
      an illumination subsystem;
      a set of adjustable lenses; and
      a controller connected to the imaging sub system, to the illumination subsystem, and to the set of adjustable lenses;
   calculating, by the controller, a histogram of pixel intensities from an image of the user's eyes captured by the imaging subsystem;
   adjusting, by the controller, an intensity of the illumination system to use an intensity by which the user's eyes are clearly discernible by the imaging subsystem;
   obtaining, by the controller, an estimate of viewing angle for each of the user's eyes, wherein the controller obtains the viewing angle of each of the user's eyes by the steps of:
      receiving a pupil image from the imaging subsystem; and
      obtaining an estimate of viewing angle from the features of the pupil image;
   calculating, in the controller, an estimated viewing distance from the estimated viewing angles of both of the user's eyes; and
   adjusting, by the controller, the focal power of each lens in the set of adjustable lenses to provide improved vision in each of the user's eyes based on a predetermined correction factor for the estimated viewing distance.

2. The method of claim 1, wherein the eyewear device is an eyeglass frame.

3. The method of claim 1, wherein the imaging subsystem comprises a camera system connected to the controller and adapted to provide the pupil image of each of the user's eyes to the controller.

4. The method of claim 3, wherein the illumination system comprises an infrared light emitting diode for each eye.

5. A self-adjusting vision system comprising:
   an eyeglass frame;
   an imaging subsystem attached to the eyeglass frame;
   an illumination subsystem attached to the eyeglass frame;
   a lens subsystem attached to the eyeglass frame;
   a controller attached to the eyeglass frame and electronically connected to the imaging subsystem, the lens subsystem and the illumination subsystem; and
   a power supply attached to the eyeglass frame and electronically connected to the controller; wherein the controller is programmed to:
      calculate a histogram of pixel intensities from an image of the user's eyes captured by the imaging subsystem;
      adjust an intensity of the illumination system to use an intensity by which the user's eyes are clearly discernible by the imaging subsystem;

obtain an estimate of viewing angle for each of the user's eyes by: (i) receiving a pupil image from the imaging subsystem; and (ii) obtaining an estimate of viewing angle from the features of the pupil image;

calculate an estimated viewing distance from the estimated viewing angles of both of the user's eyes; and adjust the focal power of each lens in the set of adjustable lenses to provide improved vision in each eye of the user's eyes based on a predetermined correction factor for the estimated viewing distance.

6. The self-adjusting vision system of claim 5, wherein the imaging subsystem comprises two CMOS sensors, each positioned to capture an image of an eye when the eyeglass frame is worn by a user.

7. The self-adjusting vision system of claim 5, wherein the illumination subsystem comprises four wide-angle infrared light sources, wherein two of said light sources are adapted to illuminate each eye.

8. The self-adjusting vision system of claim 7, wherein the infrared light sources are light emitting diodes.

9. The self-adjusting vision system of claim 5, wherein the lens subsystem comprises two adjustable lenses.

10. The self-adjusting vision system of claim 9, wherein the lens subsystem comprises an electro-mechanically adjustable lens or a liquid crystal lens.

11. The self-adjusting vision system of claim 9, wherein the self-adjusting lenses are focus tunable Alvarez lenses.

12. The self-adjusting vision system of claim 9, wherein the self-adjusting lenses are liquid crystal lenses.

13. The self-adjusting vision system of claim 9, wherein the lens subsystem further comprises a fixed lens.

* * * * *